(12) United States Patent
Freeberg

(10) Patent No.: US 8,417,341 B2
(45) Date of Patent: Apr. 9, 2013

(54) PACEMAKER RF TELEMETRY REPEATER AND METHOD

(75) Inventor: Scott Freeberg, Birchwood Village, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 36 days.

(21) Appl. No.: 13/220,830

(22) Filed: Aug. 30, 2011

(65) Prior Publication Data
US 2011/0313494 A1 Dec. 22, 2011

Related U.S. Application Data

(62) Division of application No. 11/215,453, filed on Aug. 29, 2005, now Pat. No. 8,027,727.

(51) Int. Cl.
*A61N 1/00* (2006.01)
(52) U.S. Cl. ............... 607/32; 607/30; 607/60; 128/903
(58) Field of Classification Search .................. 607/30, 607/32, 60; 128/903
See application file for complete search history.

(56) References Cited

U.S. PATENT DOCUMENTS

| | | | |
|---|---|---|---|
| 4,799,059 A | 1/1989 | Grindahl et al. | |
| 5,127,404 A | 7/1992 | Wyborny et al. | |
| 5,137,022 A | 8/1992 | Henry | |
| 5,383,915 A | 1/1995 | Adams | |
| 5,433,736 A | 7/1995 | Nilsson | |
| 5,466,246 A | 11/1995 | Silvian | |
| 5,562,713 A | 10/1996 | Silvian | |
| 5,626,630 A * | 5/1997 | Markowitz et al. | 607/60 |
| 5,720,770 A | 2/1998 | Nappholz et al. | |
| 5,720,771 A | 2/1998 | Snell | |
| 5,728,154 A | 3/1998 | Crossett et al. | |
| 5,735,887 A | 4/1998 | Barreras, Sr. et al. | |
| 5,741,315 A | 4/1998 | Lee et al. | |
| 5,752,976 A | 5/1998 | Duffin et al. | |
| 5,769,876 A | 6/1998 | Silvian | |
| 5,843,139 A | 12/1998 | Goedeke et al. | |
| 5,861,019 A | 1/1999 | Sun et al. | |
| 5,919,214 A | 7/1999 | Ciciarelli et al. | |
| 6,106,551 A | 8/2000 | Crossett et al. | |

(Continued)

OTHER PUBLICATIONS

"U.S. Appl. No. 11/215,453 Non-Final Office Action mailed Oct. 1, 2010", 9 pgs.

(Continued)

*Primary Examiner* — Nicole F Lavert
(74) *Attorney, Agent, or Firm* — Schwegman Lundberg & Woessner, P.A.

(57) ABSTRACT

A system and method for repeating radio frequency (RF) transmissions between a programmer and an implantable medical device (IMD) is provided. One aspect of this disclosure relates to an RF repeater. According to various embodiments, the repeater includes a first antenna and a first communication circuit electrically connected to the first antenna. The first communication circuit is adapted to communicate with an IMD, the IMD including a built-in active telemetry transceiver, over a first channel. The device also includes a second antenna and a second communication circuit electrically connected to the second antenna. The second communication circuit is adapted to communicate with a programmer over a second channel different from the first channel. The device also includes a control circuit coupled to the first and second communication circuits. The control circuit is adapted to enable or disable the first and second communication circuits. Other aspects and embodiments are provided herein.

20 Claims, 5 Drawing Sheets

U.S. PATENT DOCUMENTS

| | | | |
|---|---|---|---|
| 6,115,636 A | 9/2000 | Ryan | |
| 6,150,951 A | 11/2000 | Olejniczak | |
| 6,167,310 A | 12/2000 | Grevious | |
| 6,167,312 A | 12/2000 | Goedeke | |
| 6,169,925 B1 | 1/2001 | Villaseca et al. | |
| 6,223,083 B1 | 4/2001 | Rosar | |
| 6,381,492 B1 | 4/2002 | Rockwell et al. | |
| 6,400,990 B1 | 6/2002 | Silvian | |
| 6,424,867 B1 | 7/2002 | Snell et al. | |
| 6,443,891 B1 | 9/2002 | Grevious | |
| 6,456,883 B1 | 9/2002 | Torgerson et al. | |
| 6,477,424 B1 * | 11/2002 | Thompson et al. | 607/60 |
| 6,477,425 B1 | 11/2002 | Nowick et al. | |
| 6,574,510 B2 | 6/2003 | Von Arx et al. | |
| 6,622,045 B2 | 9/2003 | Snell et al. | |
| 6,631,296 B1 | 10/2003 | Parramon et al. | |
| 6,636,769 B2 | 10/2003 | Govari et al. | |
| 6,648,823 B2 * | 11/2003 | Thompson | 600/300 |
| 6,650,944 B2 | 11/2003 | Goedeke et al. | |
| 6,704,602 B2 | 3/2004 | Berg et al. | |
| 6,738,670 B1 | 5/2004 | Almendinger et al. | |
| 6,738,671 B2 | 5/2004 | Christophersom et al. | |
| 6,752,155 B2 | 6/2004 | Behm | |
| 6,763,269 B2 | 7/2004 | Cox | |
| 6,801,807 B2 | 10/2004 | Abrahamson | |
| 6,897,788 B2 | 5/2005 | Khair et al. | |
| 6,985,088 B2 | 1/2006 | Goetz et al. | |
| 6,985,773 B2 | 1/2006 | Von Arx et al. | |
| 6,993,393 B2 | 1/2006 | Von Arx et al. | |
| 7,009,511 B2 | 3/2006 | Mazar et al. | |
| 7,024,248 B2 | 4/2006 | Penner et al. | |
| 7,047,076 B1 | 5/2006 | Li et al. | |
| 7,065,409 B2 | 6/2006 | Mazar | |
| 7,069,086 B2 | 6/2006 | Von Arx | |
| 7,076,303 B2 | 7/2006 | Linberg | |
| 7,110,824 B2 | 9/2006 | Amundson et al. | |
| 7,127,300 B2 | 10/2006 | Mazar et al. | |
| 7,155,290 B2 | 12/2006 | Von Arx et al. | |
| 7,209,790 B2 | 4/2007 | Thompson et al. | |
| 7,212,133 B2 | 5/2007 | Goetz et al. | |
| 7,239,916 B2 | 7/2007 | Thompson et al. | |
| 7,270,633 B1 | 9/2007 | Goscha et al. | |
| 7,292,139 B2 | 11/2007 | Mazar et al. | |
| 7,317,946 B2 | 1/2008 | Twetan et al. | |
| 2001/0012955 A1 | 8/2001 | Goedeke et al. | |
| 2002/0123672 A1 | 9/2002 | Christophersom et al. | |
| 2002/0143372 A1 | 10/2002 | Snell et al. | |
| 2002/0183806 A1 | 12/2002 | Abrahamson et al. | |
| 2003/0097157 A1 | 5/2003 | Wohlgemuth et al. | |
| 2003/0130708 A1 | 7/2003 | Von Arx et al. | |
| 2003/0187484 A1 | 10/2003 | Davis et al. | |
| 2003/0229382 A1 | 12/2003 | Sun et al. | |
| 2003/0229383 A1 | 12/2003 | Whitehurst et al. | |
| 2004/0049246 A1 | 3/2004 | Almendinger et al. | |
| 2004/0078067 A1 | 4/2004 | Thompson et al. | |
| 2004/0127959 A1 | 7/2004 | Amundson et al. | |
| 2004/0167587 A1 | 8/2004 | Thompson | |
| 2004/0176811 A1 | 9/2004 | Von Arx et al. | |
| 2004/0176822 A1 | 9/2004 | Thompson et al. | |
| 2004/0260363 A1 * | 12/2004 | Arx et al. | 607/60 |
| 2005/0283198 A1 | 12/2005 | Haubrich et al. | |
| 2006/0100674 A1 | 5/2006 | Molin | |
| 2006/0122666 A1 | 6/2006 | Nghiem et al. | |
| 2006/0122667 A1 | 6/2006 | Chavan et al. | |
| 2007/0049983 A1 | 3/2007 | Freeberg | |
| 2007/0049992 A1 | 3/2007 | Freeberg | |
| 2007/0167994 A1 | 7/2007 | Shelton et al. | |
| 2007/0167995 A1 | 7/2007 | Dudding et al. | |
| 2007/0185546 A1 | 8/2007 | Tseng et al. | |
| 2007/0185547 A1 | 8/2007 | Hoyme et al. | |
| 2008/0009921 A1 | 1/2008 | Mosesov et al. | |
| 2008/0021521 A1 | 1/2008 | Shah et al. | |

OTHER PUBLICATIONS

"U.S. Appl. No. 11/215,453, Advisory Action mailed Dec. 23, 2008", 3 pgs.

"U.S. Appl. No. 11/215,453, Examiner Interview Summary mailed Nov. 17, 2008", 2 pgs.

"U.S. Appl. No. 11/215,453, Final Office Action mailed Apr. 15, 2010", 8 pgs.

"U.S. Appl. No. 11/215,453, Final Office Action mailed Oct. 7, 2008", 15 pgs.

"U.S. Appl. No. 11/215,453, Non Final Office Action Mailed Oct. 26, 2009", 8 pgs.

"U.S. Appl. No. 11/215,453, Non-Final Office Action mailed Feb. 22, 2008", 16 pgs.

"U.S. Appl. No. 11/215,453, Non-Final Office Action mailed Apr. 1, 2009", 7 pgs.

"U.S. Appl. No. 11/215,453, Notice of Allowance mailed May 23, 2011", 6 pgs.

"U.S. Appl. No. 11/215,453, Response filed Jan. 26, 2010 to Non Final Office Action mailed Oct. 26, 2009", 11 pgs.

"U.S. Appl. No. 11/215,453, Response filed Jan. 31, 2011 to Non Final Office Action mailed Oct. 1, 2010", 12 pgs.

"U.S. Appl. No. 11/215,453, Response filed Feb. 5, 2008 to Restriction Requirement mailed Jan. 14, 2008", 9 pgs.

"U.S. Appl. No. 11/215,453, Response filed May 22, 2008 to Non-Final Office Action mailed Feb. 22, 2008", 11 pgs.

"U.S. Appl. No. 11/215,453, Response filed Jun. 30, 2009 to Non Final Office Action mailed Apr. 1, 2009", 11 pgs.

"U.S. Appl. No. 11/215,453, Response filed Jul. 7, 2010 to Final Office Action mailed Apr. 15, 2010", 12 pgs.

"U.S. Appl. No. 11/215,453, Response filed Dec. 8, 2008 to Final Office Action mailed Oct. 7, 2008", 11 pgs.

"U.S. Appl. No. 11/215,453, Restriction Requirement mailed Jan. 14, 2008", 8 pgs.

* cited by examiner

PACEMAKER RF TELEMETRY REPEATER AND METHOD

This application is a division of and claims the benefit of priority under 35 U.S.C. §120 to U.S. patent application Ser. No. 11/215,453, filed on Aug. 29, 2005, now issued as U.S. Pat. No. 8,027,727, which is hereby incorporated by reference herein in its entirety.

TECHNICAL FIELD

This disclosure relates generally to implantable medical devices and, more particularly, to systems and methods for communicating with implantable medical devices.

BACKGROUND

Implantable medical devices (IMDs) include devices implanted in the human body to provide medical treatment. Examples include implantable pacemakers, defibrillators and heart failure devices. A device exterior to the human body, called a programmer, is used to program an IMD.

Some programmers and IMDs communicate via radio frequencies (RF) using a wireless electrical connection. The quality of the wireless communication between the programmer and the IMD, whether in an operating room, an intensive care facility, a patient follow-up clinic, or home monitoring situation, may be limited by causes such as interference from other RF sources and large transmission distance.

SUMMARY

The above-mentioned problems and others not expressly discussed herein are addressed by the present subject matter and will be understood by reading and studying this specification.

Disclosed herein, among other things, is a device for repeating RF transmissions between a programmer and an IMD. An embodiment of the device includes a first antenna and a first communication circuit electrically connected to the first antenna. The first communication circuit is adapted to communicate with an IMD, the IMD including a built-in active telemetry transceiver, over a first channel. The device also includes a second antenna and a second communication circuit electrically connected to the second antenna. The second communication circuit is adapted to communicate with a programmer over a second channel different from the first channel. An embodiment of the device also includes a control circuit coupled to the first and second communication circuits. The control circuit is adapted to enable or disable the first and second communication circuits to receive a signal from the IMD and transmit to the programmer or to receive a signal from the programmer and transmit to the IMD.

One aspect of this disclosure relates to an RF telemetry repeater. According to one embodiment, the repeater includes an IMD side and a programmer side. The IMD side includes an IMD antenna and an IMD communication circuit coupled to the IMD antenna. The IMD communication circuit is adapted to communicate with an IMD, the IMD including a built-in active telemetry transceiver, over an IMD channel. A control circuit is coupled to the IMD communication circuit. In an embodiment, the programmer side includes a programmer antenna and a programmer communication circuit coupled to the programmer antenna. The programmer communication circuit is adapted to communicate with a programmer over a programmer channel. The programmer communication circuit is also coupled to the control circuit, and the programmer is adapted to control the control circuit such that when the programmer is sending to the IMD, the programmer communication circuit receives a signal from the programmer and the IMD communication circuit transmits the signal to the IMD, and when the programmer is not sending to the IMD, the IMD communication circuit listens to the IMD.

Another aspect of this disclosure relates to a system for repeating RF transmissions between a programmer and an IMD. According to one embodiment, the system includes an IMD, the IMD including a built-in active telemetry transceiver, and a programmer wirelessly coupled to the IMD. The system also includes an RF repeater positioned to receive a RF communication between the implantable medical device and the programmer. According to an embodiment, the repeater includes a first antenna and a first communication circuit electrically connected to the first antenna. The first communication circuit is adapted to communicate with an IMD over a first channel. The device also includes a second antenna and a second communication circuit electrically connected to the second antenna. The second communication circuit is adapted to communicate with a programmer over a second channel different from the first channel. An embodiment of the device also includes a control circuit coupled to the first and second communication circuits. The control circuit is adapted to enable or disable the first and second communication circuits to receive a signal from the IMD and transmit to the programmer or to receive a signal from the programmer and transmit to the IMD.

Various system embodiments include a means for receiving a radio frequency communication between an IMD and a programmer over a first channel. Various system embodiments also include a means for transmitting the radio frequency communication over a second channel different from the first channel to improve transmission quality and reduce potential for lost or interrupted communication.

Another aspect of this disclosure relates to a method for repeating RF communications between a programmer and an IMD. An embodiment of the method includes receiving a radio frequency communication between an IMD and a programmer over a first channel. The method also includes transmitting the radio frequency communication over a second channel different from the first channel to improve transmission quality and reduce potential for lost or interrupted communication.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope of the present invention is defined by the appended claims and their legal equivalents.

DETAILED DESCRIPTION

The following detailed description refers to the accompanying drawings which show, by way of illustration, specific aspects and embodiments in which the present invention may be practiced. The various embodiments are not necessarily mutually exclusive, as aspects of one embodiment can be combined with aspects of another embodiment. These embodiments are described in sufficient detail to enable those skilled in the art to practice the invention. Other embodiments may be utilized and structural, logical, and electrical changes may be made without departing from the scope of the present invention.

IMD/Programmer System

Figure 1:
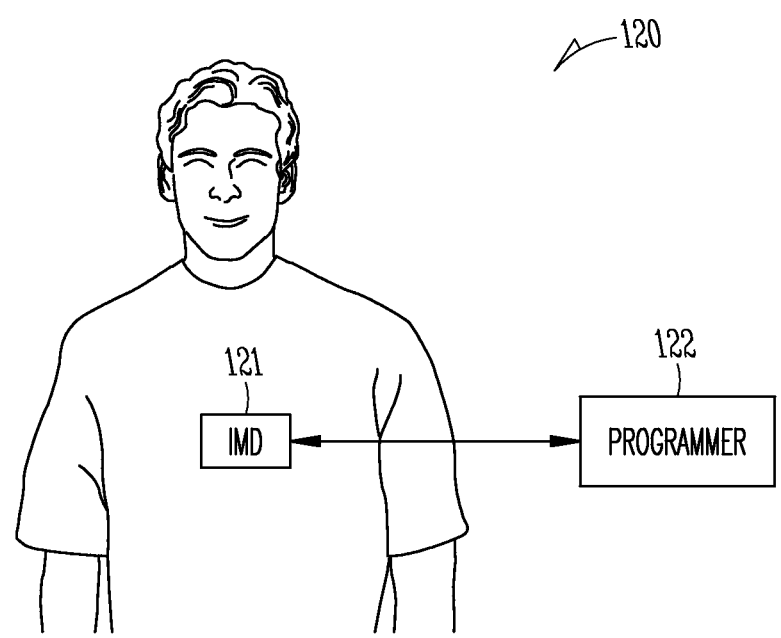
FIG. 1 illustrates a system including an implantable medical device (IMD) and a programmer, according to various embodiments.

FIG. 1 illustrates a system 120 including an implantable medical device (IMD) 121 and a programmer 122, according to various embodiments. Various embodiments of the IMD 121 include pulse generators, cardiac rhythm management devices (with pacing and defibrillating capabilities), neural stimulators, and various embodiments include a combination of neural stimulation and cardiac rhythm management functions. The programmer 122 and the IMD 121 are capable of wirelessly communicating data and instructions. In various embodiments, for example, the programmer 122 and IMD 121 use telemetry coils to wirelessly communicate data and instructions. Thus, the programmer can be used to adjust the programmed therapy provided by the IMD 121, and the IMD can report device data (such as battery and lead resistance) and therapy data (such as sense and stimulation data) to the programmer using radio telemetry, for example. The IMD includes a built-in active telemetry transceiver, according to various embodiments. In some embodiments, the IMD includes built-in active telemetry transmitter and receiver.

Figure 2:
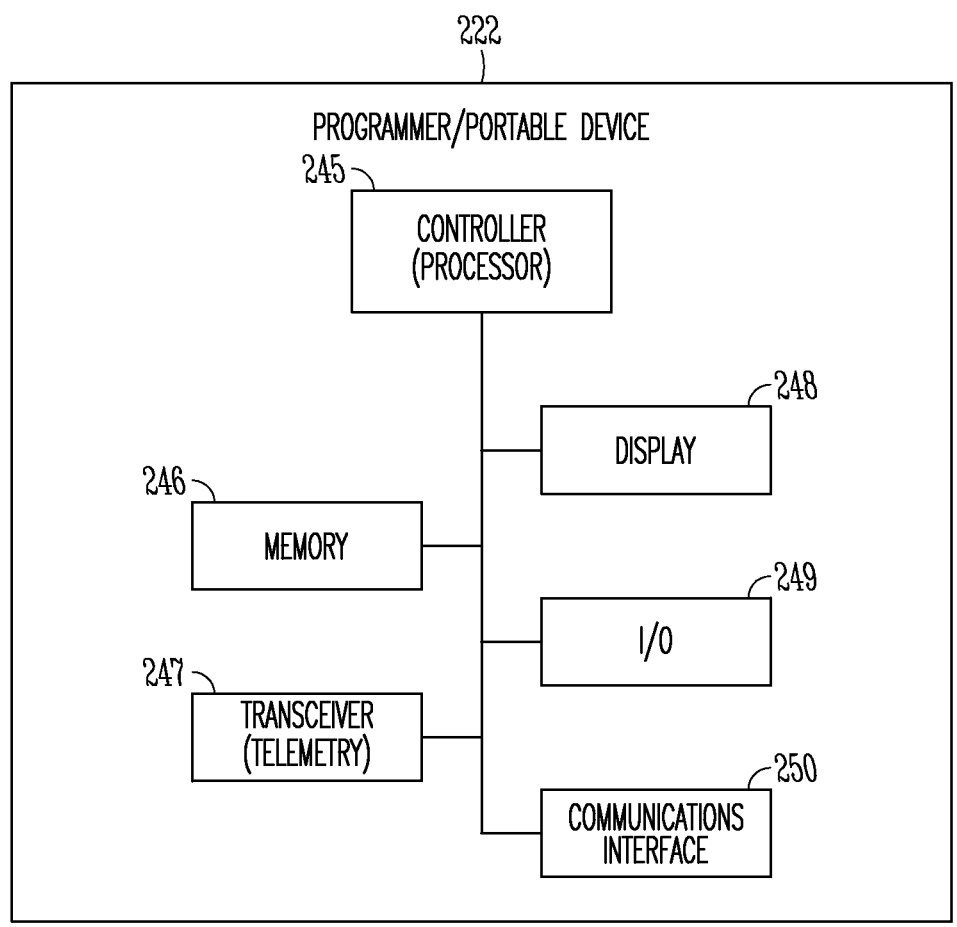
FIG. 2 illustrates a programmer such as illustrated in the system of FIG. 1 or other external device to communicate with the IMD(s), according to various embodiments.

FIG. 2 illustrates a programmer 222, such as the programmer 122 illustrated in the system of FIG. 1 or other external device to communicate with the IMD(s), according to various embodiments. An example of another external device includes Personal Digital Assistants (PDAs) or personal laptop and desktop computers in an Advanced Patient Management (APM) system. The illustrated device 222 includes controller circuit 245 and a memory 246. The controller circuit 245 is capable of being implemented using hardware, software, and combinations of hardware and software. For example, according to various embodiments, the controller circuit 245 includes a processor to perform instructions embedded in the memory 246 to perform a number of functions, including communicating data and/or programming instructions to the implantable devices. The illustrated device 222 further includes a transceiver 247 and associated circuitry for use to communicate with an implantable device. Various embodiments have wireless communication capabilities. For example, various embodiments of the transceiver 247 and associated circuitry include a telemetry coil for use to wirelessly communicate with an implantable device. The illustrated device 222 further includes a display 248, input/output (I/O) devices 249 such as a keyboard or mouse/pointer, and a communications interface 250 for use to communicate with other devices, such as over a communication network.

As mentioned above, the quality of the wireless communication between the programmer and the IMD, whether in an operating room, an intensive care facility, a patient follow-up clinic, or home monitoring situation, may be limited by causes such as interference from other RF sources and large transmission distance.

RF Telemetry Repeater

The disclosed RF telemetry repeater is a device that can extend the telemetry quality and telemetry distance between an RF enabled IMD and a programmer. The RF repeater can receive a transmission from the IMD and retransmit the signal to the programmer, and vice versa. By increasing the strength of the signal upon retransmission, the quality of the telemetry transmission can be improved and the potential for lost signals ("drop-outs") can be reduced.

Figure 3:
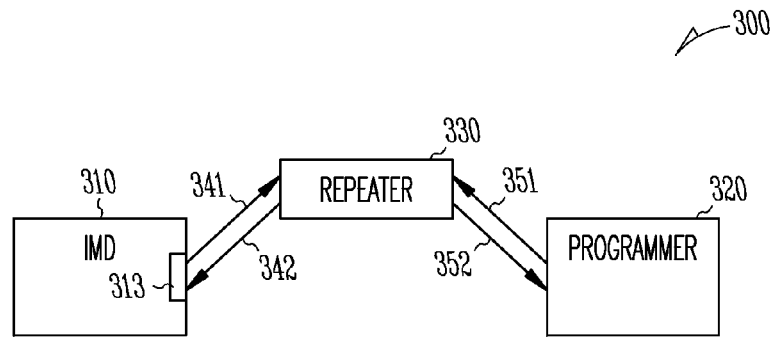
FIG. 3 illustrates a system including a repeater, a programmer and an IMD, according to various embodiments.

FIG. 3 illustrates a system 300 including a repeater 330, a programmer 320 and an IMD 310, according to various embodiments. The repeater 330 can receive an IMD to programmer transmission along an IMD receive channel 341, and retransmits the transmission along a programmer transmit channel 351. The repeater 330 can also receive a programmer to IMD transmission along a programmer receive channel 352, and retransmits the transmission along an IMD transmit channel 342. The channels may use the same or different frequencies in various embodiments. As the repeater 330 can use a different frequency or channel for communicating with the IMD than with the programmer, interference can be reduced and throughput increased. The repeater has the capability to be enabled or disabled by the programmer to allow the programmer to select direct programmer-IMD communications or programmer-repeater-IMD communications. The IMD includes built-in active telemetry equipment 313. In an embodiment, the telemetry equipment includes a transmitter and receiver. In some embodiments, the telemetry equipment includes a transceiver.

The repeater can be placed on the ceiling or wall of a clinic or operating room, placed on a tray or table, or can be a hand-held unit in various embodiments. When the repeater is at a higher physical location than the IMD or the programmer, better line of sight communication is facilitated. The repeater can be engaged at the request of the programmer or the IMD when the link quality is marginal, according to various embodiments.

Figure 4:
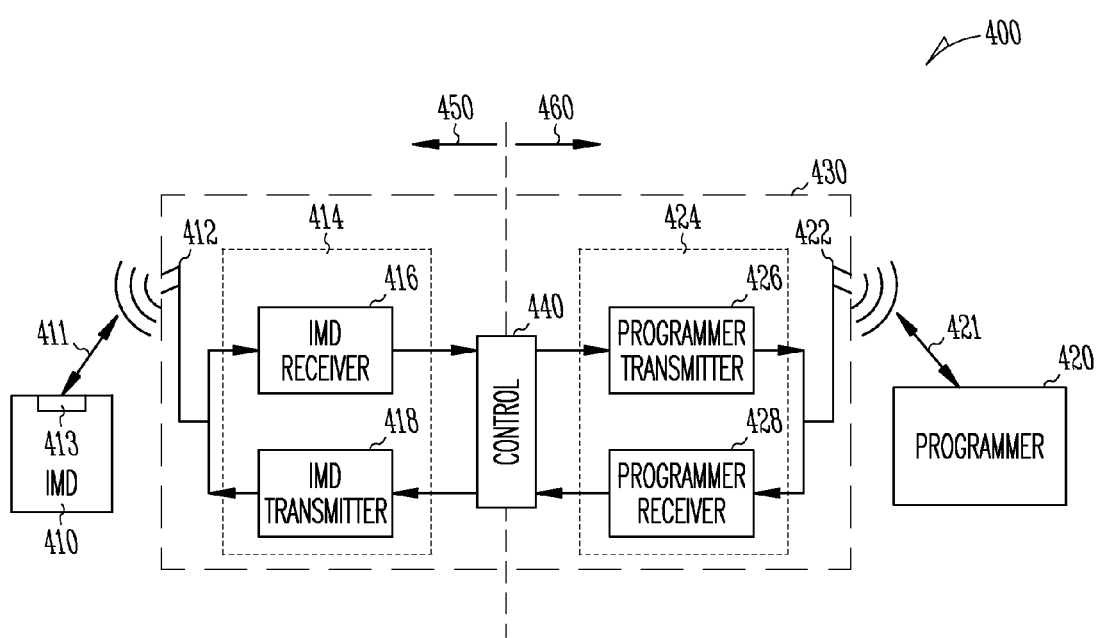
FIG. 4 illustrates a system for repeating RF transmissions between a programmer and an IMD, according to various embodiments.

FIG. 4 illustrates a system for repeating RF transmissions between a programmer and an IMD, according to various embodiments. The system 400 includes an IMD 410, a programmer 420 wirelessly coupled to the IMD 410, and a radio frequency repeater device 430 positioned to receive a radio frequency communication between the IMD and the programmer. An embodiment of the device 430 includes a first antenna 412 and a first communication circuit 414 electrically connected to the first antenna. The first communication circuit 414 is adapted to communicate with an IMD 410 over a first channel 411. The device 430 also includes a second antenna 422 and a second communication circuit 424 electrically connected to the second antenna. The second communication circuit 424 is adapted to communicate with a programmer 420 over a second channel 421 different from the first channel. An embodiment of the device also includes a control circuit 440 coupled to the first and second communication circuit. The control circuit is adapted to enable or disable the first and second communication circuits to receive a signal from the IMD 410 and transmit to the programmer 420 or to receive a signal from the programmer 420 and transmit to the IMD 410. The control circuit effectively regenerates and transmits the received signal. The control circuit 440 can be used to turn on or off receive circuitry or transmit circuitry based on multiple inputs.

According to various embodiments, the first communication circuit 414 includes a first receiver 416 and a first transmitter 418. The first communication circuit may alternatively include a first transceiver. According to various embodiments, the second communication circuit 424 includes a second receiver 428 and a second transmitter 426. The second communication circuit may alternatively include a second transceiver. The control circuit 440 includes logic adapted to determine when the programmer is sending data to the IMD or receiving data from the IMD. The device 430 can send data to the IMD when the programmer is in a sending mode. When the programmer stops sending data, the control circuit stops transmitting to the IMD and assumes a listening mode. When the IMD starts sending data, the device will receive the data and turn on the programmer-side transmitter to send that data to the programmer. When the IMD has stopped sending data, the control circuit stops transmitting to the programmer and assumes a listening mode. The control circuit includes a microprocessor in an embodiment. In various embodiments, the control circuit includes a filter to prevent transmitted signals from being picked up on the other side of the repeater.

In one embodiment, the first channel 411 includes a first frequency and the second channel 412 includes a second frequency different from the first frequency. The programmer 420 is adapted to control the control circuit 440 in an embodiment, such that when the programmer is sending a transmission to the IMD 410, the second communication circuit 424 receives a signal from the programmer 420 and the first communication circuit 414 transmits the signal to the IMD 410, and when the programmer 420 is not sending to the IMD 410, the first communication circuit listens to the IMD. The programmer 420 is further adapted to select a frequency of communication with the repeater that differs from the frequency of communication with the IMD, to avoid interference. In one embodiment, the programmer 420 is adapted to control the control circuit 440 to disable the device 430 to allow direct communications from the programmer to the IMD and from the IMD to the programmer.

The device 430 can be separated into an IMD side 450 and a programmer side 460. The IMD side includes the first antenna 412 and first communication circuit 414. The programmer side includes the second antenna 422 and the second communication circuit 424. The sides share the control circuit 440 in various embodiments. In various embodiments, the repeater device 430 is self-contained, with its own power supply, and does not require any network or digital connections. The IMD includes a built-in active telemetry transceiver 413 in various embodiments.

As an example of a repeated transmission, the IMD transmits a signal to the repeater. The signal is received by the repeater IMD receiver 416. The repeater control circuit 440 processes the signal and turns on the repeater programmer transmitter 426. Data is then transmitted to the programmer.

Figure 5:
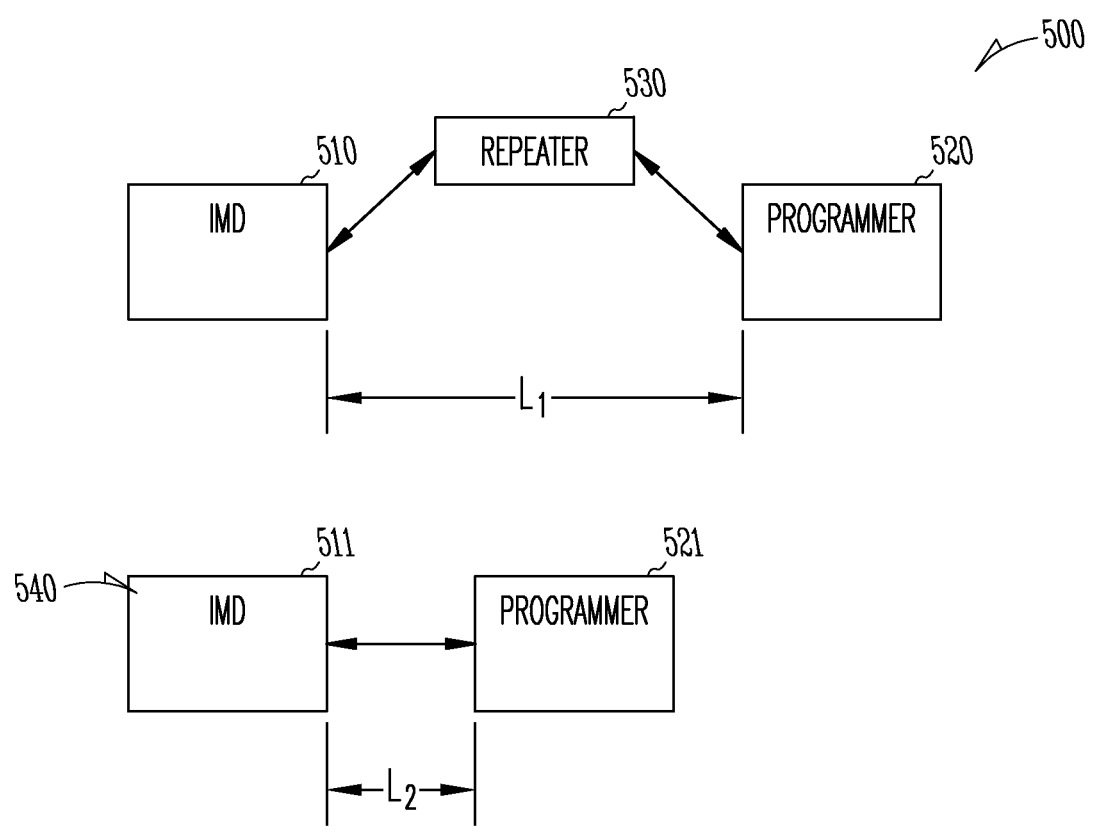
FIG. 5 illustrates improved telemetry distance using an RF repeater, according to various embodiments.

FIG. 5 illustrates improved telemetry distance using an RF repeater, according to various embodiments. A system 540 including an IMD 511 and programmer 521 with a wireless connection is illustrated. The maximum transmission distance in this configuration is $L_2$. A second system 500 adds the disclosed repeater 530 in position to receive and retransmit communications between an IMD 510 and programmer 520. The maximum transmission distance in this configuration is $L_1$. As shown, the repeater 530 provides the ability to increase the telemetry transmission distance between an IMD and a programmer. In addition, the repeater provides the ability to increase the reliability and quality of an RF link. In an embodiment, the programmer and IMD use different frequencies to communicate with the repeater, to reduce the potential for interference and drop outs.

Monitoring IMD/Programmer Communications

Figure 6:
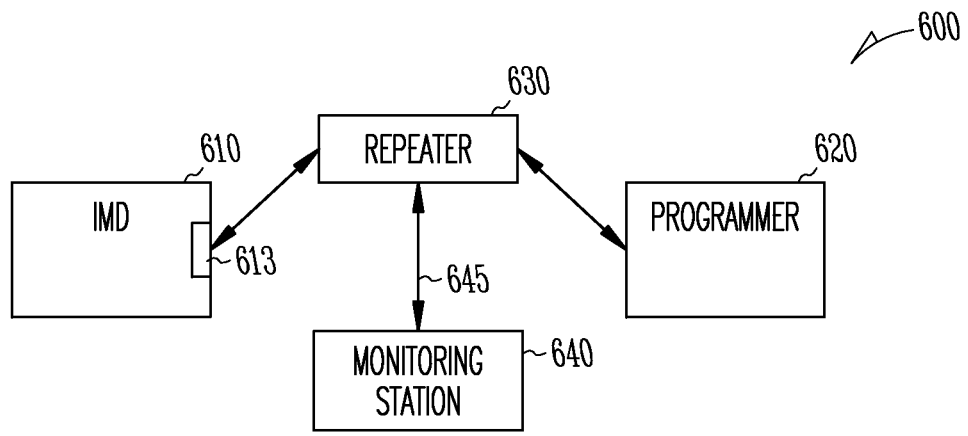
FIG. 6 illustrates a system including a programmer, an IMD, and an RF repeater including a network connection, according to various embodiments.

FIG. 6 illustrates a system 600 including a programmer 620, an IMD 610, and an RF repeater 630 including a network connection, according to various embodiments. The IMD includes a built-in active telemetry transceiver 613 in various embodiments. In the illustrated configuration, the repeater 630 acts as a data intercept. A connection 645 to a monitoring station 640 allows the repeated data to be intercepted and routed to a network, which provides for data monitoring capability. The connection 645 is adapted to receive data transmitted between the programmer and the IMD and forward the data to the monitoring station 640. The monitoring station may be part of an Advanced Patient Monitoring (APM) system, in an embodiment.

In one embodiment, the monitoring station 640 includes a website. The monitoring station 640 includes a local area network, in an embodiment. The monitoring station 640 may also include a personal computer. Other types of monitoring stations are within the scope of this disclosure. In various embodiments, the connection 645 includes an Ethernet connection. The connection 645 may also include a Universal Serial Bus (USB) communication link in an embodiment. Those of skill in the art will understand that other types of connections are within the scope of this disclosure.

Method for Repeating IMD/Programmer Communications

Figure 7:
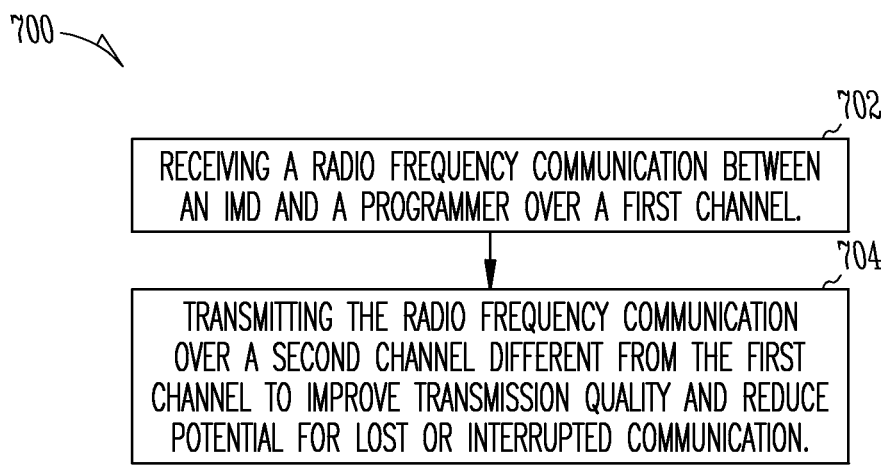
FIG. 7 illustrates a flow diagram of a method for repeating RF communications between a programmer and an IMD, according to various embodiments.

FIG. 7 illustrates a flow diagram of a method for repeating RF communications between a programmer and an IMD, according to various embodiments. The method 700 includes receiving a radio frequency communication between an IMD and a programmer over a first channel, at 702. The method also includes transmitting the radio frequency communication over a second channel different from the first channel to improve transmission quality and reduce potential for lost or interrupted communication, at 704.

According to various embodiments, the method 700 includes receiving the radio frequency communication at a first frequency and transmitting the radio frequency communication at a second frequency different from the first frequency. The method also includes transmitting the radio frequency communication from a higher elevation than either the IMD or the programmer, in an embodiment. In various embodiments, the method includes transmitting the radio frequency communication at amplitude sufficient to improve transmission quality and reduce potential for lost or interrupted communication compared to direct communication between the IMD and the programmer. The method further includes forwarding data received in the radio frequency communication to a monitoring station, in various embodiments. In one embodiment, forwarding data received in the radio frequency communication to a monitoring station includes forwarding data to a website. In another embodiment, forwarding data received in the radio frequency communication to a monitoring station includes forwarding data to a local area network.

One of ordinary skill in the art will understand that, the modules and other circuitry shown and described herein can be implemented using software, hardware, and combinations of software and hardware. As such, the illustrated modules and circuitry are intended to encompass software implementations, hardware implementations, and software and hardware implementations.

The methods illustrated in this disclosure are not intended to be exclusive of other methods within the scope of the present subject matter. Those of ordinary skill in the art will understand, upon reading and comprehending this disclosure, other methods within the scope of the present subject matter. The above-identified embodiments, and portions of the illustrated embodiments, are not necessarily mutually exclusive. These embodiments, or portions thereof, can be combined. In various embodiments, the methods provided above are implemented as a computer data signal embodied in a carrier wave or propagated signal, that represents a sequence of instructions which, when executed by a processor cause the processor to perform the respective method. In various embodiments, methods provided above are implemented as a set of instructions contained on a computer-accessible medium capable of directing a processor to perform the respective method. In various embodiments, the medium is a magnetic medium, an electronic medium, or an optical medium.

Although specific embodiments have been illustrated and described herein, it will be appreciated by those of ordinary skill in the art that any arrangement which is calculated to achieve the same purpose may be substituted for the specific embodiment shown. This application is intended to cover adaptations or variations of the present subject matter. It is to be understood that the above description is intended to be illustrative, and not restrictive. Combinations of the above embodiments as well as combinations of portions of the above embodiments in other embodiments will be apparent to those of skill in the art upon reviewing the above description. The scope of the present subject matter should be determined with reference to the appended claims, along with the full scope of equivalents to which such claims are entitled.

What is claimed is:

1. A method, comprising:
    using a programmer to activate a repeater device to receive a radio frequency communication between a therapy-providing implantable medical device (IMD) and the programmer over a first channel;
    using the repeater device to transmit the radio frequency communication over a second channel different front the first channel to improve transmission quality and reduce potential for lost or interrupted communication; and
    using the programmer to deactivate the repeater device to allow direct communications from the programmer to the IMD and from the IMD to the programmer.

2. The method of claim 1, wherein receiving a radio frequency communication includes receiving the radio frequency communication at a first frequency.

3. The method of claim 2, wherein transmitting the radio frequency communication includes transmitting the radio frequency communication at a second frequency different from the first frequency.

4. The method of claim 1, wherein transmitting the radio frequency communication includes transmitting the radio frequency communication from a higher elevation than either the IMD or the programmer.

5. The method of claim 1, wherein transmitting the radio frequency communication includes transmitting the radio frequency communication at an amplitude sufficient to improve transmission quality and reduce potential for lost or interrupted communication compared to direct communication between the IMD and the programmer.

6. The method of claim 1, further comprising:
    forwarding data received in the radio frequency communication to a monitoring station.

7. The method of claim 6, wherein forwarding data received in the radio frequency communication to a monitoring station includes forwarding data to a website.

8. The method of claim 6, wherein forwarding data received in the radio frequency communication to a monitoring station includes forwarding data to a local area network.

9. The method of claim 1, wherein receiving a radio frequency communication includes using the programmer to control the receiving.

10. The method of claim 1, wherein transmitting the radio frequency communication includes using the programmer to control the transmitting.

11. A method for using a radio frequency telemetry repeater having a first communication circuit and a second communication circuit, the method comprising:
    using a programmer to activate the repeater;
    receiving a first radio frequency communication from a therapy-providing implantable medical device (IMD) over a first channel using the first communication circuit;
    transmitting the first radio frequency communication to the programmer over a second channel different from the first channel using the second communication circuit;
    receiving a second radio frequency communication from the programmer using the second communication circuit;
    transmitting the second radio frequency communication to the IMD using the first communication circuit; and
    using the programmer to deactivate the repeater to allow direct communications from the programmer to the IMD and from the IMD to the programmer.

12. The method of claim 11, further comprising determining when the programmer is sending data to the IMD or receiving data from the IMD.

13. The method of claim 12, further comprising, upon determining that the programmer is sending data to the IMD, enabling the second communication circuit to receive and the first communication circuit to transmit.

14. The method of claim 12, further comprising, upon determining that the programmer is not sending data to the IMD, enabling the first communication circuit to receive and the second communication circuit to transmit.

15. The method of claim 11, wherein transmitting the first radio frequency communication includes increasing signal strength of the received first communication.

16. The method of claim 11, wherein transmitting the second radio frequency communication includes increasing signal strength of the received second communication.

17. The method of claim 11, wherein receiving and transmitting using the first communication circuit includes using a first transceiver.

18. The method of claim 11, wherein receiving and transmitting using the first communication circuit includes using a first transmitter and a first receiver.

19. The method of claim 11, wherein receiving and transmitting using the second communication circuit includes receiving using a second transceiver.

20. The method of claim 11, wherein receiving and transmitting using the second communication circuit includes using a second transmitter and a second receiver.

* * * * *